United States Patent [19]

Inomata et al.

[11] Patent Number: 5,254,699
[45] Date of Patent: Oct. 19, 1993

[54] CYCLIC PERFLUOROETHERS AND METHOD OF MAKING

[75] Inventors: Hiroshi Inomata, Annaka; Yasuo Tarumi, Takasaki; Noriyuki Koike, Tano; Shuzi Suganuma, Takasaki, all of Japan

[73] Assignee: Shin-Etsu Chemical Co., Ltd., Tokyo, Japan

[21] Appl. No.: 868,767

[22] Filed: Apr. 16, 1992

[30] Foreign Application Priority Data

Apr. 16, 1991 [JP] Japan .................. 3-111100

[51] Int. Cl.$^5$ ............................ C07D 319/12
[52] U.S. Cl. .................. 549/380; 549/352; 549/353
[58] Field of Search ............ 549/380, 347, 352, 353

[56] References Cited

U.S. PATENT DOCUMENTS

| | | | |
|---|---|---|---|
| 3,250,807 | 5/1966 | Fritz et al. | 560/227 |
| 3,321,517 | 5/1967 | Salman | 549/380 |
| 4,067,884 | 1/1978 | Martini | 549/380 |
| 4,343,742 | 8/1982 | Muffler et al. | 549/380 |
| 4,686,024 | 8/1987 | Scherer et al. | 549/347 |
| 4,736,045 | 4/1988 | Drakesmith et al. | 549/380 |

OTHER PUBLICATIONS

Abe et al, Chem. Abst., vol. 86, #43134q (1977).
J. A. Semlyen, "Cyclic Polymers", Elsevier Applied Science Publishers.
J. March, "Advanced Organic Chemistry" (1975).

Primary Examiner—James H. Reamer
Attorney, Agent, or Firm—Millen, White, Zelano, & Branigan

[57] ABSTRACT

Provided are novel cyclic perfluoroethers which are thermally and chemical stable fluids. They are prepared by photo decarbonylation of cyclic perfluoroketones.

3 Claims, No Drawings

CYCLIC PERFLUOROETHERS AND METHOD OF MAKING

This invention relates to novel cyclic perfluoroethers and a method for making the same.

BACKGROUND OF THE INVENTION

Perfluorodioxane derivatives known in the art include perfluoroethyl-1,4-dioxane and perfluoropropyl-1,4-dioxane of the following formulae as reported in WO 84/02909 by ICI.

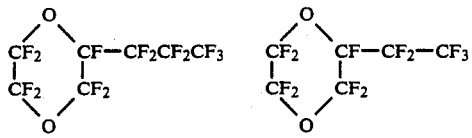

These compounds are stable fluids useful as heat pump media, solvents and heat transfer media.

These compounds, however, suffer from a serious problem in their manufacture. More particularly, the perfluoroethyl derivatives are synthesized by a process as shown by the following scheme.

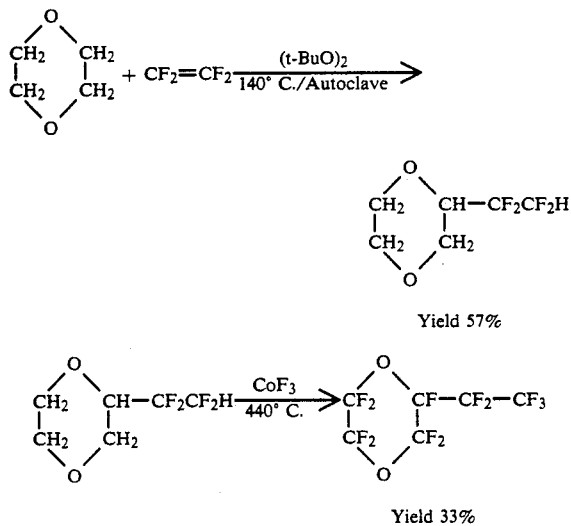

This process involves high-temperature radical reaction in an autoclave and fluorination reaction with $CoF_3$ at very high temperatures. The reaction can be commercially practiced always with difficulty with respect to safety management, reaction control, and synthesis equipment cost. Especially the fluorinating agent $CoF_3$ must be prepared using $F_2$ gas, which requires extremely careful operation

SUMMARY OF THE INVENTION

Therefore, an object of the present invention is to provide novel cyclic perfluoroethers including perfluorodioxane derivatives.

Another object of the present invention is to provide a novel method for synthesizing cyclic perfluoroethers under moderate conditions in high yields.

The inventors have found that by reacting a perfluorodicarboxylic acid difluoride of formula (3) with a carbonate salt in an aprotic solvent, the acid fluorides at both ends are condensed into cyclic form through mild ionic reaction to form a novel cyclic perfluoroketone of formula (2). The cyclic perfluoroketone of formula (2) is then exposed to ultraviolet radiation at room temperature or lower for decarbonylation, giving a novel cyclic perfluoroether of formula (1) under moderate conditions in high yields.

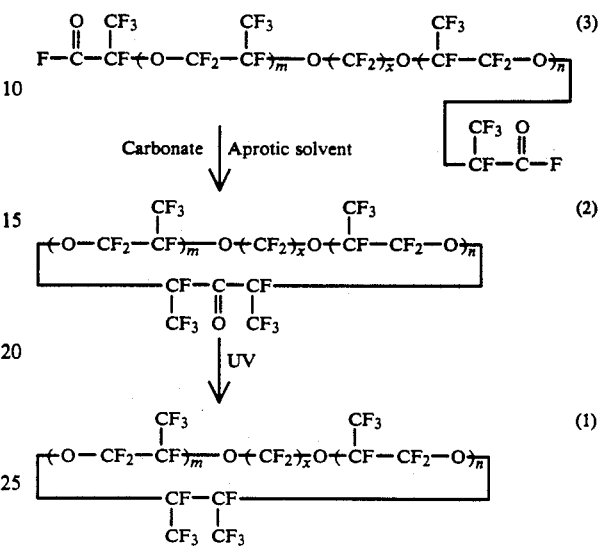

In the formulae, x is an integer of from 2 to 10, and m and n are independently an integer of from 0 to 2.

The cyclic perfluoroethers of formula (1) are thermally and chemically very stable liquids and useful as leak test fluids in the semiconductor industry, dielectric fluids in electric equipment, reaction solvents in the chemical industry, heat transfer media in heat exchangers and the like.

DETAILED DESCRIPTION OF THE INVENTION

The present invention provides novel cyclic perfluoroethers of formula (1). They are prepared by first reacting perfluorodicarboxylic acid difluorides of formula (3) with carbonate salts in an aprotic polar solvent to form novel cyclic perfluoroketones of formula (2) as an intermediate, and then exposing the ketones to ultraviolet radiation to form the desired ethers.

The carbonates used herein are represented by the general formula $M_2CO_3$ wherein M is selected from the group consisting of Li, Na, K, Rb, Cs, and Ag, with $Na_2CO_3$ and $K_2CO_3$ being preferred. Use of anhydrous carbonate salts is preferred in order to control undesired side reaction. It is thus recommended to remove water from the carbonate salts by heating or vacuum drying prior to use.

The aprotic polar solvents used herein include amides such as dimethylformamide, dimethylacetamide, and hexa. methylphosphoric triamide; and ethers such as diethyl ether, tetrahydrofuran, dioxane, ethylene glycol dimethyl ether (glyme), diethylene glycol dimethyl ether (diglyme), triethylene glycol dimethyl ether (triglyme), and tetraethylene glycol dimethyl ether (tetraglyme), with the diglyme, triglyme and tetraglyme being preferred. It is also recommended to remove water from the solvents prior to use.

Though not bound to the theory, it is believed that the conversion of the perfluorodicarboxylic acid difluorides of formula (3) into the cyclic perfluoroketones of formula (2) proceeds through the process that the acid fluoride at one molecular end of the perfluorodicarboxylic acid difluoride first reacts with a carbonate to form a carboxylate which, in turn, reacts with the acid fluoride at the other end to form a cyclic ketone. This process is illustrated by the following chemical scheme.

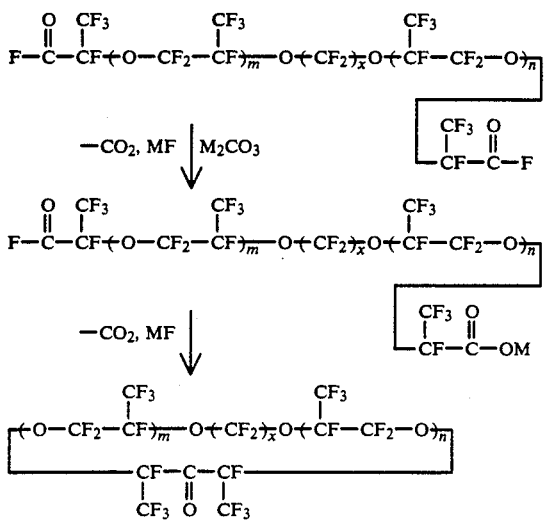

In the formulae, x is an integer of from 2 to 10, and m and n are independently an integer of from 0 to 2.

The molar ratio of the carbonate to the perfluorodicarboxylic acid difluoride used is 1:1 from a stoichiometric aspect, but it is preferable in practice to use the carbonate in excess for reaction efficiency. For better results, the carbonate and the perfluorodicarboxylic acid difluoride are used in a molar ratio of from 1.2/1 to 5.0/1. If the amount of the carbonate used exceeds this range, there is the risk that undesirably both the ends of the molecule become carboxylates. The amount of the solvent used is not critical although it is often used in an amount of about 0.2 to 20 liters per mole of the perfluoro-dicarboxylic acid difluoride.

Reaction may be effected by adding dropwise the perfluorodicarboxylic acid difluoride to a mixture of the carbonate and the solvent, preferably at a temperature of 20° to 200° C. At the end of addition, it is sometimes necessary to heat the reaction mixture to a temperature of 100° to 200° C. for increasing the conversion rate of the reactant, preferably to a temperature of 150° to 200° C. for optimum reaction rates. The progress of reaction can be monitored by infrared spectroscopy wherein the absorption of acid fluoride appearing near 1890 $cm^{-1}$ diminishes and eventually disappears. The reaction pressure is not critical and may be atmospheric or under pressure in an autoclave. Atmospheric pressure is convenient because reaction is accompanied by evolution of carbon dioxide gas. At the end of reaction, the product or cyclic perfluoroketone may be isolated by distillation. It is possible to sequentially distill out the product as it is produced during reaction The cyclic perfluoroether of formula (1) are then produced by exposing the thus obtained cyclic perfluoroketone of formula (2) to ultraviolet radiation for decarbonylation. The reaction scheme is shown below.

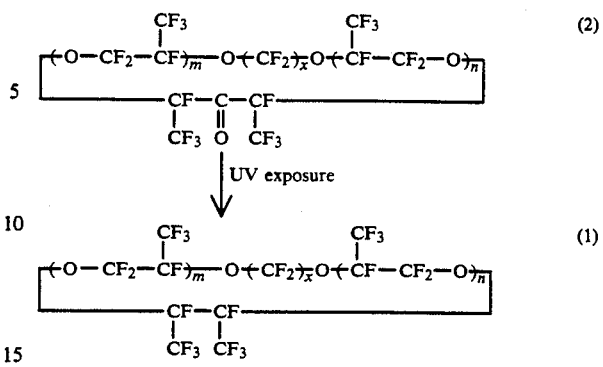

This process may be conducted in accordance with the technique disclosed in Japanese Patent Application Kokai No. 10209/1977 by Hoechst. The preferred UV source used in a high-pressure mercury lamp of quartz having a maximum output at a wavelength of 300 to 600 nm which is often effective in this type of reaction. For exposure, the cyclic perfluoro-ketone alone or a solution thereof in a solvent which does not virtually absorb UV light is exposed to a high-pressure mercury lamp while the lamp is cooled with water or air for removing heat therefrom. Reaction is preferably carried out in an atmosphere of an inert gas, for example, nitrogen or argon gas. For promoting reaction, it is effective to agitate the reaction solution during exposure. The reaction temperature is not critical although near room temperature is preferred because higher temperatures can induce undesirable side reaction. The process of reaction can be monitored by infrared spectroscopy wherein the absorption of ketone appearing at 1790 $cm^{-1}$ diminishes and eventually disappears or gas chromatography wherein the peak corresponding to the reactant diminishes and eventually disappears. Usually, it takes 10 to 500 hours to complete the reaction. At the end of light exposure, the cyclic perfluoroether of the invention may be readily isolated in highly pure form from the reaction solution by distillation.

EXAMPLE

Examples of the present invention are given below by way of illustration and not by way of limitation.

EXAMPLE 1

A 3-liter glass reactor equipped with a stirrer, a distillation head connected to a condenser and a cock for distilling out the product, a thermometer, and a heating bath was charged with 500 ml of dry diglyme and 424 grams (4 mol) of dry sodium carbonate. Reaction was conducted in a nitrogen gas stream by adding dropwise 426 grams (1 mol) of perfluoro-2,7-dimethyl-3,6-dioxasuberic acid difluoride of the following formula (4) to the reactor at a temperature of 80° C. over one hour.

At the end of addition, the temperature was raised to 150° C. and the reactor was maintained at the temperature for 3 hours while allowing the product to distill out. The crude product was distilled under atmospheric pressure, yielding 171 grams (0.48 mol) of perfluoro-2,7-dimethyl-3,6-dioxacycloheptanone of the following formula (5) having a boiling point of 84° C. The following structure was established by the analytical data.

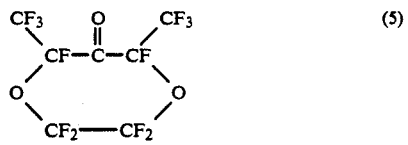
(5)

IR spectrum: 1790 cm$^{-1}$ $^{19}$F-NMR spectrum: The chemical shifts are relative to CF$_3$COOH. Two values were observed probably because two trifluoromethyl groups formed cis and trans isomers.

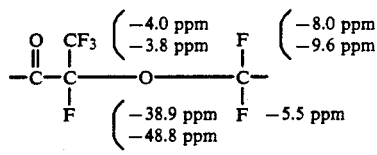

$^{13}$C-NMR spectrum: The chemical shifts are relative to TMS. Two values were observed for the same reason as above.

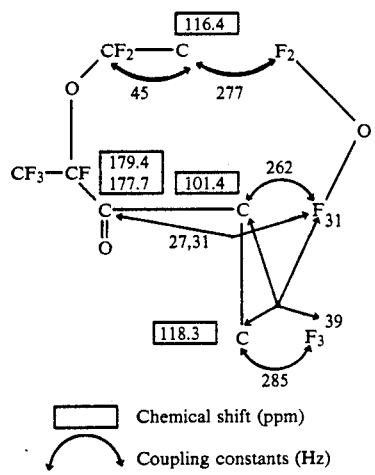

Mass spectrum:
341 (M-F)
263 CF$_3$—CF—O—CF$_2$—O—CF
132 O—CF$_2$—CF$_2$—O
100 C$_2$F$_4$

|    | Elemental analysis: | |
|----|---------------------|--------|
|    | Calcd. | Found |
| C: | 23.4% | 23.7% |
| F: | 63.3% | 62.5% |

Next, a 100-ml glass reactor equipped with UVL-100HA high-pressure mercury lamp (manufactured by Riko Kagaku Sangyo K.K.) was charged with 175 grams (0.49 mol) of the above obtained perfluoro-2,7-dimethyl-3,6-dioxacycloheptanone. The reactor was also equipped with a dry ice condenser and a magnetic stirrer, and argon gas was slowly passed therethrough. After 190 hours of UV exposure, the disappearance of the reactant was observed by gas chromatography. There was obtained 146.5 grams (yield 81%) of a crude product having a purity of 89%. Distillation yielded 104.5 grams of a fraction having a boiling point of 65° C. with a purity of higher than 97%. This product was identified to be perfluoro-2,3-dimethyl-1,4-dioxane of the following formula (6) by the analytical data.

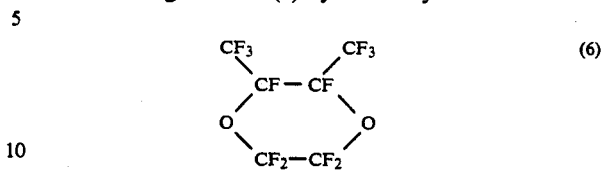
(6)

IR spectrum: No absorption appeared at wave numbers higher than 1400 cm$^{-1}$, indicating the absence of ketone and other functional groups.

$^{19}$F-NMR:
−3 to −21 ppm 10F (CF$_3$, —CF$_2$—)
−49 to −51 ppm 2F (—CF—)

The chemical shifts are relative to CF$_3$COOH.

Mass spectrum: 313 (M-F), 263 (M-CF$_3$)

Elemental analysis:

|    | Elemental analysis: | |
|----|---------------------|--------|
|    | Calcd. | Found |
| C: | 21.7% | 21.1% |
| F: | 68.7 | 67.9% |

The cyclic perfluoroethers of the invention are thermally and chemically very stable liquids and useful as leak test fluids in the semiconductor industry, dielectric fluids in electric equipment, reaction solvents in the chemical industry, heat transfer media in heat exchangers and the like. The method of the invention can produce such cyclic perfluoroethers under moderate conditions in high yields, with commercial advantages.

Although some preferred embodiments have been described, many modifications and variations may be made thereto in the light of the above teachings. It is therefore to be understood that within the scope of the appended claims, the invention may be practiced otherwise than as specifically described.

We claim:

1. A cyclic perfluoroether of the general formula (1):

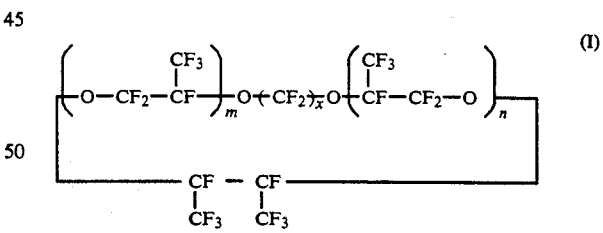
(I)

wherein x is an integer of from 2 to 10, and m and n are independently an integer of from 0 to 2.

2. A cyclic perfluoroether of the general formula (1):

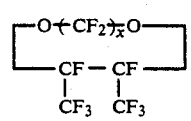

wherein x is an integer of from 2 to 10.

3. A cyclic perfluoroether of claim 1, wherein x is 2, m is 0 and n is 0.

* * * * *